(12) United States Patent
Lal et al.

(10) Patent No.: US 10,174,154 B2
(45) Date of Patent: Jan. 8, 2019

(54) AMIDOPOLYAMINES WITH ENHANCED GEL-TIME FOR ELEVATED TEMPERATURE APPLICATIONS

(71) Applicant: EVONIK DEGUSSA GMBH, Essen (DE)

(72) Inventors: Gauri Sankar Lal, Whitehall, PA (US); Sudhir Ananthachar, Hillsborough, NJ (US); Stephen Michael Boyce, Bath, PA (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/932,095

(22) Filed: Nov. 4, 2015

(65) Prior Publication Data

US 2016/0122467 A1    May 5, 2016

Related U.S. Application Data

(60) Provisional application No. 62/074,727, filed on Nov. 4, 2014.

(51) Int. Cl.
| | | |
|---|---|---|
| *C08G 59/54* | (2006.01) | |
| *C09D 163/00* | (2006.01) | |
| *C07C 233/38* | (2006.01) | |

(52) U.S. Cl.
CPC ............ *C08G 59/54* (2013.01); *C07C 233/38* (2013.01); *C09D 163/00* (2013.01)

(58) Field of Classification Search
CPC .................................................. C08G 59/54
See application file for complete search history.

(56) References Cited

U.S. PATENT DOCUMENTS

| | | | | |
|---|---|---|---|---|
| 3,280,140 | A * | 10/1966 | Sharkey ................. | C08G 69/34 548/312.7 |
| 3,468,904 | A * | 9/1969 | Kritchevsky ......... | C07D 233/14 516/68 |
| 5,214,155 | A * | 5/1993 | Hollingsworth ..... | C07D 233/24 548/347.1 |
| 5,948,881 | A * | 9/1999 | Shah .................. | C08G 59/5026 524/100 |
| 6,046,282 | A * | 4/2000 | Starner ................. | C08G 59/54 525/432 |
| 2012/0237774 | A1* | 9/2012 | Raymond ............. | C08G 59/44 428/418 |
| 2015/0094400 | A1* | 4/2015 | Zheng ................... | C08G 59/60 523/222 |
| 2015/0197682 | A1* | 7/2015 | Treybig ................. | C09K 8/32 507/117 |
| 2017/0306067 | A1* | 10/2017 | Kurth .................... | C08F 210/02 |

FOREIGN PATENT DOCUMENTS

| | | |
|---|---|---|
| EP | 1024159 A1 | 8/2000 |
| WO | 2008076211 A1 | 6/2008 |

* cited by examiner

*Primary Examiner* — Megan McCulley
(74) *Attorney, Agent, or Firm* — Andrew H. Chung; Linda S. Li; Jason S. Ngui

(57) ABSTRACT

An epoxy curing agent is disclosed that can be obtained by reacting at least one carboxylic acid with at least one polyamine. The disclosed curing agent can be obtained by preparing an amidoamine with about 0.15 to about 0.30 molar excess of carboxylic acid.

9 Claims, No Drawings

AMIDOPOLYAMINES WITH ENHANCED GEL-TIME FOR ELEVATED TEMPERATURE APPLICATIONS

This application claims the benefit of Application No. 62/074,727, filed on Nov. 4, 2014. The disclosure of Application No. 62/074,727 is hereby incorporated by reference.

BACKGROUND OF THE INVENTION

The instant invention relates to epoxy curing agents and, in particular to epoxy curing agents comprising amidopolyamines.

Amidopolyamines are known to be used as curing agents for epoxy resins and typically are low viscosity amber-colored liquids. The advantages of amidopolyamines over conventional curing agents include reduced volatility, reduced skin-irritation, more convenient mixing ratios, increased flexibility and impact strength in the cured products. Examples of conventional curing agents are described in H. Lee and K. Neville in Handbook of Epoxy Chemistry, McGraw Hill book company © 1967, p. 10-2 to 10-3); hereby incorporated by reference.

Generally, in a composition having a short pot life, a reaction abruptly occurs and the time to reach the cured state is short, whereas in a composition having a long pot life, the time necessary for curing is relatively long. As a result, there is a need in this art for a liquid epoxide-based composition having as long a pot life as several tens of hours and being curable at relatively low temperature range (moderate temperature range) of 60-100° C. Such a composition comprising an epoxide and curing agent both being a liquid would enable paint coatings to be conveniently applied at ambient temperatures without premature cure.

BRIEF SUMMARY OF THE INVENTION

The instant invention solves problems associated with conventional amidoamine curing agents by providing a curing agent having improved pot-life that cures a relatively low temperature.

The pot life of the inventive amidoamine curing agents varies with imidazoline content. Curing agents having a relatively high imidazoline content offer longer pot life but also decreases reactivity of epoxy cure. When the imidazoline content of a curing agent is too high the epoxy cure becomes impractical for commercial applications. The instant invention relates to a curing agent having a defined imidazoline/amide ratio that can be used to cure an epoxy resin that imparts a surprisingly enhanced latency at room temperature but cures rapidly at elevated temperatures (e.g., about 60 to about 90° C.).

The inventive curing agent can be obtained by reacting at least one carboxylic acid with at least one polyamine. In particular, the inventive curing agent is obtained by preparing an amidoamine with about 0.15 to about 0.30 molar excess of carboxylic acid relative to polyamines at temperatures above 190° C. in order to maximize the imidazoline/amide ratio. Examples of suitable carboxylic acids comprise at least one member selected from the group consisting of octanoic acid, 2-ethylhexanoic acid, decanoic acid, dodecanoic acid, and tall oil fatty acid and dimer fatty acid. Examples of suitable polyamines comprise at least one member selected from the group consisting of polyethyleneamines (EDA, DETA, TETA, TEPA, PEHA, and the like), dipropylenetriamine, polypropyleneamines (dipropylenetriamine), N-3-aminopropyl ethylenediamine (N3), aminopropylated ethylenediamines (Am3, Am4, Am5, and the like), aminopropylated propylenediamines, 1,6-hexanediamine (HMDA), 3,3,5-trimethyl-1,6-hexanediamine, tripropylenetetramine, N-3-aminopropyl-1,3-diaminopropane, N,N'-bis(3-aminopropyl)-1,3-diaminopropane, N,N,N'-tris(3-aminopropyl)-1,3-diaminopropane, 2-methyl-1,5-pentanediamine, N,N'-bis(3-aminopropyl) ethylenediamine (N4), N,N,N'-tris(3-aminopropyl) ethylenediamine (N5), and any combination thereof.

The inventive curing agent can be obtained by reacting at least one carboxylic acid with at least one polyamine. In particular, the inventive curing agent is obtained by preparing an amidoamine with about 0.15 to about 0.30 molar excess of carboxylic acid relative to polyamines at temperatures above 190° C. in order to maximize the imidazoline/amide ratio. Examples of suitable carboxylic acids comprise at least one member selected from the group consisting of octanoic acid, 2-ethylhexanoic acid, decanoic acid, dodecanoic acid, and tall oil fatty acid and dimer fatty acid. Examples of suitable polyamines comprise at least one member selected from the group consisting of polyethyleneamines (EDA, DETA, TETA, TEPA, PEHA, and the like), dipropylenetriamine, polypropyleneamines (dipropylenetriamine), N-3-aminopropyl ethylenediamine (N3), aminopropylated ethylenediamines (Am3, Am4, Am5, and the like), aminopropylated propylenediamines, 1,6-hexanediamine (HMDA), 3,3,5-trimethyl-1,6-hexanediamine, tripropylenetetramine, N-3-aminopropyl-1,3-diaminopropane, N,N'-bis(3-aminopropyl)-1,3-diaminopropane, N,N, N'-tris(3-aminopropyl)-1,3-diaminopropane, 2-methyl-1,5-pentanediamine, N,N'-bis(3-aminopropyl) ethylenediamine (N4), N,N,N'-tris(3-aminopropyl) ethylenediamine (N5), and any combination thereof.

The reaction to prepare the inventive curing agent involves heating a polyamine while in the presence of the carboxylic acid at a temperature ranging from about 150 to about 250° C. with removal of water formed during the reaction.

A comparison of amidoamines of TOFA with DETA shows that when the ratio of DETA to TOFA is about 1:1.15 to about 1:1.30 the latency or gel time as measured by the increase in viscosity to 20,000 cP is increased by two to three times than when prepared from DETA to TOFA with a molar ratio of 1:1. Similar results were obtained with the amidoamine prepared from TETA and TOFA. In addition the rate of cure as measured by the time for complete hardness development at 65° C. was essentially unchanged.

One aspect of the invention relates to an epoxide-based composition, comprising:
(A) an epoxide component comprising at least one phenyl glycidyl ether polyepoxide having at least two epoxide group of oxirane structure in the molecule.
(B) A curing agent component comprising an amidoamine of a polyamine with tall oil fatty acid which is obtained by reacting one molar equivalent of the polyamine with 1.15-1.30 molar equivalent of tall oil fatty acid.

One aspect of the invention relates to the foregoing aspect, wherein the mixture of the epoxide component and curing agent do not show an increase in viscosity of greater than about 20,000 cP within about 11 to about 30 h of mixing.

Another aspect of the invention relates to the foregoing aspects wherein the mixture of the epoxide component and curing agent is cured completely at a temperature at about 60 to about 100° C.

Another aspect of the invention relates to the foregoing aspects wherein the mixture of the epoxide component and curing agent is used to prepare epoxy coatings that are cured completely at about 60 to about 100° C.

DETAILED DESCRIPTION OF THE INVENTION

The following definitions are used in the instant specification: "Curing" means toughening or hardening of an epoxy resin by cross-linking of polymer chains, brought about by a curing agent such as an amine, thiol carboxylic acid, alcohols and carboxylic acid anhydrides and is measured by the increase in viscosity over time by a viscometer.

"Curing Temperature" means the temperature at which complete cure takes place and is measured by a viscometer or visual observation of hardness of the finished material. The inventive curing agent can cure an epoxy resin at a temperature of about 60° C. to about 100° C., about 70° C. to about 90° C. and in some cases about 65° C. to about 85° C.

"Gel Time" means the thickening of an epoxy after it is mixed and heated to an elevated temperature. Gel Time is measured by a viscometer and by visual observation of the formation of a non-flowing gel. The inventive curing agent can be combined with an epoxy resin wherein the combination has a gel time of about 16 h to about 36 h, about 36 h to about 20 h and in some cases about 30 h to about 36 h at a temperature of about 60° C. to about 100° C.

"Latent Curing" means a curing agent which is stable in an admixture with the epoxy resin at ambient temperature and effect hardening only when heated to elevated temperatures, and is measured by its viscosity change at ambient temperature.

"Pot Life" means the amount of time available to apply the product after mixing. Pot life depends also on the temperature and amount of product, and is measured by the change in viscosity over time. In this application pot life refers to a viscosity increase to 20,000 cP at 25° C. The inventive curing agent can be combined with an epoxy resin wherein the combination has a pot-life of about 20 h to about 30 h, about 24 h to about 30 h, and in some cases about 16 h to about 20 h at temperature of about 25° C. to about 30° C.

Amidopolyamines can be derived from monobasic carboxylic acids and aliphatic polyamines. Examples of suitable acids comprise at least one member selected from the group consisting of C16, C18, and C19 types derived from fats and oils particularly soya, tall oil and ricinoleic acids. Examples of suitable polyamines can comprise at least one member selected from the group consisting of diethylenetriamine (DETA), triethylenetetramine (TETA) and tetraethylenepentamine (TEPA).

In one aspect of the invention, the inventive amidopolyamine has a structure of:

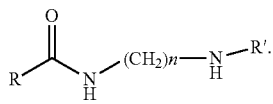

R=alkyl chain of 8-20 carbon atoms n=2-3, R'=polyalkylamine chain with or without an imidazoline ring.

The inventive amidopolyamine has a viscosity ranging from about 200 cP to about 1500 cP, about 1000 cP to about 1200 cP and about 500 cP to about 1000 cP at a temperature 25° C. when measured with a viscometer.

The inventive amidopolyamine has an equivalent weight (amine H equivalent weight) of about 20 to about 300.

One aspect of the invention relates to a reaction of the acid group of the fatty acid comprising with the amine group of a polyamine comprising polyethyleneamine thereby producing an amidopolyamine. The reaction can occur between about 150° C. to about 250° C. and typically starting at 150° C. Without wishing to be bound by any theory or explanation, it is believed that the reaction of polyethyleneamines with carboxylic acids produces the inventive amidopolymer at lower temperature but because of the proximity of the amino group to the carboxamide ring-closure can take place to generate an imidazoline structure. This reaction is favored at temperatures less than about 200° C. Thus, the ratio of imidazoline to amide in the amidopolyamine reaction product can be controlled by adjusting the reaction temperature and time. A higher imidazoline content gives lower viscosity and lower reactivity with epoxy groups as well as increase the compatibility of the curing agent with epoxy resins and other materials high in aromatic content or in hydrocarbon characteristics.

Examples of epoxy resins that can be cured by the inventive curing agent comprise at least one member selected from the group consisting of a phenyl glycidyl ether epoxide having a plurality of oxirane structures in the molecule and having reactivity with an amine, and examples thereof may comprise the following: Aromatic diglycidyl ethers generated by reacting diphenols such as bisphenol A, bisphenol F, bisphenol AD, tetramethylbisphenol A, tetramethyl bisphenol F or biphenyl, with epichlorohydrin; glycidyl ether obtained by reacting a novolak such as phenol novolak, cresol novolak, ethylphenol novolak, propylphenol novolak, butylphenol novolak, pentylphenol novolak, octylphenol novolak or nonylphenol novolak, with epichlorohydrin; and glycidyl ethers obtained by reacting a polyhydric phenol such as catechol, resorcinol, trihydroxybiphenyl, dihydroxybenzophenone, bisresorcinol, hydroquinone, tris(hydroxyphenyl) methane, tetrakis(hydroxyphenyl) ethane or bisphenol, with epichlorohydrin and mixtures thereof. The curing agent and epoxy resin can be combined by any suitable method such as pouring, stirring, and pumping. The ratio of epoxy resin to the inventive curing agent can range from about 5:1 to about 1:1, about 2:1 to about 3:1 and in some cases about 0.5:1 to about 1:1.

In one aspect of the invention, the inventive curing agent can be combined with at least one member selected from the group consisting of phenolic or imidazole accelerators. The amount of the foregoing members can comprise about 0.2 wt % to about 5 wt %, about 2 wt % to about 5 wt % and in some cases about 1 to about 5 wt % relative to the curing agent.

The epoxy resin and curing agent of the invention can be used in a wide range of applications including coatings and composites. In one aspect of the invention, the epoxy resin and curing agent are employed for making a coating including coatings applied onto the interior of pipes in accordance with processes known in this art. For example, a coating of the instant invention can be used for repairing pipelines for transporting water. An example of a such a coating comprises about 100 parts resin to about 80 parts of the curing agent.

EXAMPLES

The following Examples are provided to illustrate certain aspects of the invention and shall not limit the scope of the claims appended hereto. These Examples are a comparison of amidoamines of TOFA with DETA which illustrate that when the ratio of DETA to TOFA is 1:15-1:1.30 the latency or gel time as measured by the increase in viscosity to 20,000 cP is increased by two to three times than when prepared from DETA to TOFA with a molar ratio of 1:1. Similar results were obtained with the amidoamine prepared from TETA and TOFA. In addition the rate of cure as measured by the time for complete hardness development at 65° C. was essentially unchanged.

Example 1

Procedure for Preparation of Amidoamines of Polyamines with 0.15 Molar Excess TOFA A polyamine (1.0 mole) comprising Diethylenetriamine (DETA (supplied by Air Products)) was charged into a reaction kettle equipped with thermocouple, nitrogen inlet and condenser. The polyamine was then treated with the tall oil fatty acid (1.15 mole—supplied by Air Products). The mixture was heated to 225° C. and held at this temperature until water was completely distilled. The mixture was cooled to room temperature.

Example 2

Procedure for Preparation of Amidoamines of Polyamines with 0.30 Molar Excess TOFA.

A polyamine (1.0 mole) comprising Diethylenetriamine (DETA (supplied by Air Products)) was charged into a reaction kettle equipped with thermocouple, nitrogen inlet and condenser. The polyamine was then treated with the tall oil fatty acid (1.30 mole). The mixture was heated to 225° C. and held at this temperature until water was completely distilled. The mixture was cooled to room temperature.

Example 3: Latency of Amine Curatives

The curing agent of Example 1 (amount determined by its AHEW) is mixed with 100 g of bis-phenol A diglycidyl ether (EPON® 828 epoxy) using a spatula in a 200 mL glass jar. 15 g. of the mixture is transferred into a disposable aluminum chamber (Brookfield HT-2DB). A disposable aluminum spindle (Brookfield SC4-27D) is inserted into the chamber containing curing agent mixture and the Start viscometer (Brookfield RVDV-II+Pro) is stated to collect data points at the rate of 1 per minute. Pot-life is recorded as the time (hours) to reach 20,000 cP at 25° C. Complete Cure is determined by visual observation and hardness to touch. Table 1 summarizes the results of this study.

TABLE 1

Latency study of amidoamine curing agents

| Curing agent | 65° C. cure time (h) | Time to 20,000 cp (h) | Imidazoline/ Amide ratio |
|---|---|---|---|
| DETA | 2 | 10 | 1.37 |
| DETA 1.15 eq. TOFA | | | |
| DETA 1.15 eq. TOFA + 1% K-54 | 2 | 22 | 0.82 |
| DETA 1.15 eq. TOFA + 1% AMI-1 | 3 | 27 | 0.82 |
| DETA 1.30 eq. TOFA | 5 | 31 | 0.81 |
| TETA | 2 | 11.25 | 3.25 |
| TETA + 0.15 eq. TOFA | 2 | 19.45 | 4.44 |

Example 4: Coatings Application of Amidoamine Curing Agents

| | 100 Anc 3419 + 0.15 mol TOFA | 86 Anc 3419 + 0.15 mol TOFA 86PHR | |
|---|---|---|---|
| Mixed Viscosity (cps) | 993.75 | | |
| Gel Time (min) | 1866 | | |
| Induction Time | 90 minutes | | |
| Thin film Tack free, through cure and dryhard | No data | Tack free, through cure and dry hard time could not be determined due to long latency of curing agent | |
| DSC (wet) | | | |
| Onset Temp (° C.) | 88.67 | | |
| 2nd Onset Temp (° C.) | 186.36 | | |
| Peak Temp (° C.) | 125.72 | | |
| 2nd Peak Temp (° C.) | 237.61 | | |
| ΔH (J/g) | 69.4 | | |
| 2nd ΔH (J/g) | 87.83 | | |
| Tg, wet (° C.) | 50.44 | | |
| DSC (puck) | 2 hrs 85° C. | | |
| Tg, puck (° C.) | 45.66 | | |
| Onset Temp (° C.) | 55.45 | | |
| Peak Temp (° C.) | 63.06 | | |
| ΔH (J/g) | 2.39 | | |
| Tg, puck (° C.) 10 days RT | 53.44 | | |
| 20° Gloss | 93 | | |
| Peroz hardness (Clear) cured @ 25 C. for 7 days | 29 | | |
| Peroz hardnes (Clear) cured at 85 C. for 2 hours + 7 days of cure at 25 C. | 193 | | |

High Solids- Low VOC white coating

| | Lbs | Gallons |
|---|---|---|
| Liquid Epoxy Resin EEW 180-190 | 346 | 35.81 |
| Xylene | 100 | 13.97 |
| Thixatrol ST | 4 | 0.47 |
| | | 50.24 |
| Component B | | |
| Ancamide 4319 + −0.15 mole TOFA) | 312 | 39.80 |
| Tio2 Ti-Pure R 960 | 300 | 9.24 |
| Butanol | 6 | 0.89 |
| Nuosperse 657 | 3 | 0.39 |
| | 621 | 50.31 |
| Non Volatile by volume | 76.04 | |
| PVC | 12.22 | |
| VOC (Lbs/gallon) | 1.05 | |
| 20° Gloss | 74 | |
| Peroz Hardness (2 hours at 85 C) + 7 days of cure at 25 C. | 85 | |

Mixed Viscosity: Mixed viscosity of EPON 828 resin+ Curing agent as measured using Brookfield RVTD viscometer and #4 spindle @ 25° C. according to ASTM D 445-83 test method. The mixed viscosity=993.75 cps and preferred viscosity is 500-1000 cps and most preferred viscosity is 800-995 cps.

Gel time: Gel time was measured using 5. Techne GT-3 Gelation timer, 150 g mix according to ASTM D2471-1999, Standard Test Method for Gel Time and Peak Exothermic Temperature of Reacting Thermosetting Resins.

DSC of wet and cured samples: Tg was measured using Differential Scanning Calorimetry (DSC): ASTM E1356, "Standard Test Method for Assignment of the Glass Transition Temperature by Differential Scanning Calorimetry".

Gloss: Gloss was measured using Gloss meter according to ASTM D-523

Persoz hardness: Persoz was measured by ASTM D4366-14 Standard Test Methods for Hardness of Organic Coatings by Pendulum Damping Tests.

While the invention has been described with reference to certain aspects or embodiments, it will be understood by those skilled in the art that various changes may be made and equivalents may be substituted for elements thereof without departing from the scope of the invention. In addition, many modifications may be made to adapt the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An epoxide-based composition, comprising
   (A) an epoxide component comprising at least one phenyl glycidyl ether polyepoxide having at least two epoxide group of oxirane structure in the molecule;
   (B) a curing agent component comprising an amidoamine of a polyamine with tall oil fatty acid which is obtained by reacting one molar equivalent of the polyamine with about 1.30 molar equivalent of tall oil fatty acid, wherein the polyamine is selected from the group consisting of diethylenetriamine, triethylenetetramine, and tetraethylenepentamine;
   wherein the composition has an imidazoline to amide ratio of about 0.8, and wherein the composition has a viscosity of less than about 20,000 cP within about 24 hours to about 30 hours of combining the epoxide component and the curing agent component.

2. The composition of claim 1 wherein the composition has a curing temperature of about 65° C.

3. The composition of claim 1 prepared by a process comprising the steps of reacting at least one carboxylic acid with at least one polyamine.

4. The composition of claim 1 wherein the curing time is about 5 hours.

5. The composition of claim 4 wherein the cured composition has a viscosity of at least 20,000 cP.

6. A method for producing a curing agent comprising reacting at least one carboxylic acid with at least one polyamine selected from the group consisting of diethylenetriamine, triethylenetetramine, and tetraethylenepentamine;
   wherein about 0.30 molar excess of carboxylic acid to polyamines is reacted at a temperature above 190° C., and wherein the curing agent has an imidazoline to amide ratio of about 0.8.

7. The method of claim 6 wherein the carboxylic acid comprise at least one member selected from the group consisting of octanoic acid, 2-ethylhexanoic acid, decanoic acid, dodecanoic acid, tall oil fatty acid and dimer fatty acid.

8. The method of claim 6 wherein the polyamine further comprises at least one member selected from the group consisting of dipropylenetriamine, polypropyleneamines, N-3-aminopropyl ethylenediamine, aminopropylated ethylenediamines, aminopropylated propylenediamines, 1,6-hexanediamine, 3,3,5-trimethyl-1,6-hexanediamine, tripropylenetetramine, N-3-aminopropyl-1,3-diaminopropane, N,N'-bis(3-aminopropyl)-1,3-diaminopropane, N,N,N'-5 tris (3-aminopropyl)-1,3-diaminopropane, 2-methyl-1,5-pentanediamine, N,N'-bis(3-aminopropyl) ethylenediamine (N4), N,N,N'-tris(3-aminopropyl) ethylenediamine (N5), and any combination thereof.

9. The method of claim 6 wherein the curing agent has a structure of:

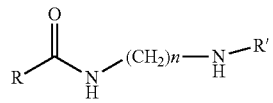

R=alkyl chain of 8-20 carbon atoms, n=2-3, R'=polyalkylamine chain with or without an imidazoline ring.

* * * * *